US00PP30318P2

(12) United States Plant Patent
Hansen

(10) Patent No.: US PP30,318 P2
(45) Date of Patent: Mar. 26, 2019

(54) ***COLOCASIA* PLANT NAMED 'BLACK SWAN'**

(50) Latin Name: ***Colocasia* hybrid**
Varietal Denomination: Black Swan

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,163

(22) Filed: Feb. 14, 2018

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new cultivar of *Colocasia* plant named 'Black Swan' characterized by large, lustrous, dark greyed-purple leaves; stemless, vigorous, tropical, perennial habit and multiple long spadix flowers surrounded by enrolled burgundy spathes.

1 Drawing Sheet

Botanical classification: *Colocasia* hybrid.
Cultivar designation: 'Black Swan'.

CROSS REFERENCE TO RELATED APPLICATIONS

This application is co-pending with the U.S. Plant Patent Applications for two other plants from the same breeding program with the same parents, namely, *Colocasia* plant named 'Black Goblet' (U.S. Plant patent application Ser. No. 15/932,772) and *Colocasia* plant named 'Distant Memory' (U.S. Plant patent application Ser. No. 15/932,164).

BACKGROUND OF THE PLANT

The present invention relates to a new and distinct hybrid of *Colocasia*, hereinafter referred to by its cultivar name, 'Black Swan'. *Colocasia* is a tropical genus in the Araceae family.

The new cultivar was derived from a controlled breeding program under the direction of by the inventor at a wholesale perennial nursery in Zeeland, Mich., USA. The overall purpose of the breeding program was to make selections of *Colocasia* plants with colorful foliage, good growth rate and that are well suited for landscape or containers. 'Black Swan' arose from a cross performed in May 17, 2012 between *Colocasia* 'Black Coral' U.S. Plant Pat. No. 23,896 as the female and the male parent was 'Thailand Giant' (not patented). 'Black Swan' was given the breeder code 12-07-01 prior to naming.

Asexual propagation of the new cultivar was first accomplished by in vitro propagation using shoot tip culture in 2014. To those skilled in the art shoot tip tissue culture produces propagules of identical characteristics to those of the original plant. Asexual propagation of 'Black Swan' by shoot tip tissue culture has shown that the characteristics of the new cultivar are stable and reproduce true to type in successive generations.

No plants of *Colocasia* 'Black Swan' have been sold, in this country or anywhere in the world, prior to the filing of this application, nor has any disclosure of the new plant been made prior to the filing of this application except that which was disclosed within one year of the filing of this application, and was either derived directly or indirectly from the inventor.

SUMMARY OF THE INVENTION

Plants of *Colocasia* 'Black Swan' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of the new plant and distinguish it as a new and distinct *Colocasia* different from all other *Colocasia* known to the inventor:

1. Large, lustrous, dark greyed-purple leaves;
2. Large, upright, stemless, vigorous, tropical perennial habit;
3. Multiple, long, spadix per leaf axil.
4. Solitary growth habit with rare basal shoot development.

BRIEF DESCRIPTION OF THE DRAWINGS

The photograph of the new plant demonstrates the unique traits and the overall appearance of *Colocasia* 'Black Swan'. The colors are as accurate as reasonably possible with color reproductions of this type. Variations in ambient light spectrum, source and direction may cause the appearance of minor variation in color. The plants used in the photograph were two-year-old plants grown initially in a greenhouse then set out early summer in a shaded trial garden at a wholesale perennial nursery in Zeeland, Mich. with supplemental water and fertilizer when needed. No plant growth regulators or pinching have been used.

Figure 1:
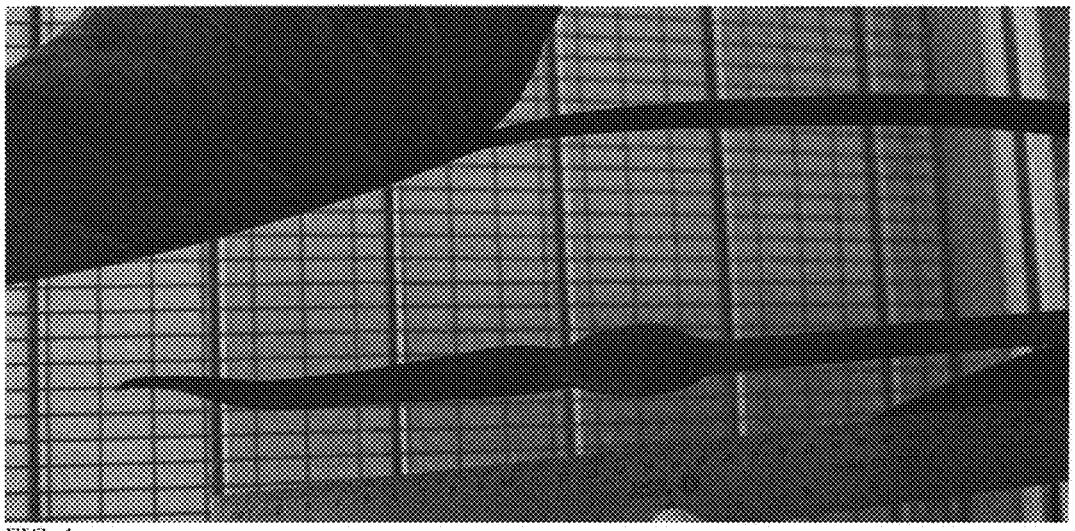
FIG. 1 shows a close-up of the flower with ruler for size reference.
Figure 2:
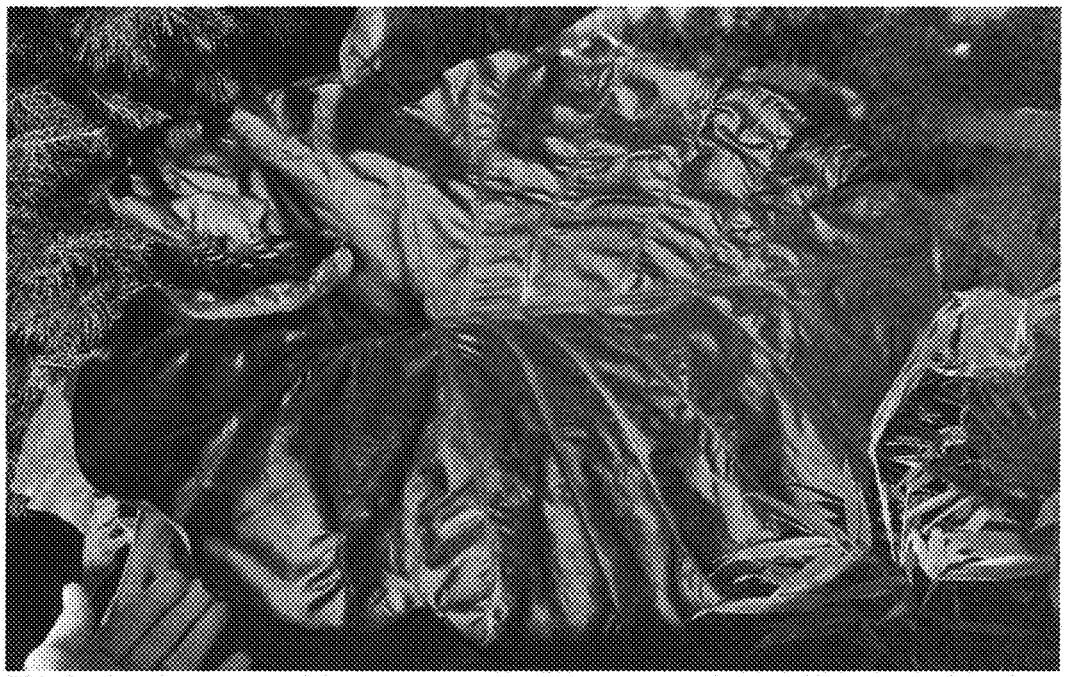
FIG. 2 shows a fully grown leaf with the shine and slight undulations and dimpling.

The nearest comparison varieties known to the inventor are the co-pending siblings and 'Black Sapphire Gecko'.

In comparison to the female parent the new plant is larger in habit and individual leaf blades are held more horizontal. 'Black Coral' also produces great numbers of basal shoots. In comparison to the green-leafed male parent the new plant is shorter with smaller leaves, has darker leaf blades and petioles and a lustrous adaxial leaf surface.

'Black Swan' has larger leaf blades than 'Black Sapphire Gecko' and leaves are held more outright and less cernuous than 'Black Sapphire Gecko'. Compared with 'Distant Memory' the new plant has more lustrous upper leaf surfaces and is larger in habit with fewer basal side shoots. Compared with 'Black Goblet' the new plant has a flatter and less cupped leaf, and the leaves are larger and darker greyed-purple.

DETAILED BOTANICAL DESCRIPTION

The following is a detailed description of two-year-old plants of the new cultivar as grown initially in a greenhouse and then outdoors for the summer of the second season, in a shaded trial garden in Zeeland, Mich. No plant growth regulators have been used. Plants of the new cultivar have not been tested under all possible conditions. The phenotype may vary with changes in environmental, climatic, and cultural conditions without change however in the genotype. The color reference is in accordance with the 2015 edition of The Royal Horticultural Society Colour Chart except where general color dictionary terms are used.

Botanical designation: *Colocasia* hybrid;

Cultivar denomination: 'Black Swan';

Parentage: The female or seed parent is 'Black Coral' and the male or pollen parent is 'Thailand Giant';

Asexual propagation: Shoot tip tissue culture;

Time to initiate roots: About two weeks;

Time to finish in a 7 liter container: About three months from a 2.5 cm plug;

Growth rate: Vigorous;

Plant habit: Tropical herbaceous perennial; upright; acaulescent; upright; clumping; tuberous rhizomes formed at base of plant;

Plant size: About 180.0 cm tall and about 160 cm wide at edges of leaves;

Root description: Thick, limited branching; to about 25.0 cm long;

Root color: Between RHS 182A and RHS 183D;

Foliage: Simple; alternate; petiolate; sagittate to cordate; slightly and irregularly undulate; slightly dimpled; base cordate to auriculate, lobes frequently imbricate; apex broadly acute to slightly cuspidate; margin entire; adaxial surface lustrous; abaxial dull; both adaxial and abaxial glabrous;

Leaf size: Average about 84.0 cm long and about 62.0 cm across; base fused about 13.5 cm below petiole attachment; basal auricles extending about 30.0 cm below petiole;

Leaf attitude: Outwardly to semi-drooping in maturity;

Leaf color: Mature adaxial blend between RHS N187A and RHS N189A under greenhouse conditions and nearest RHS N186A in trial garden, mature abaxial blend between RHS 189A and RHS 177C under greenhouse conditions and blend between RHS 146A and RHS 187A in trial garden;

Veins: Pinnate; glabrous abaxial and adaxial; main veins broad, nearly smooth adaxial and costate and rounded abaxial; abaxial midrib to about 19 mm across, lateral pinnate veins to about 4.0 mm across and secondary veins less than 0.3 mm across; adaxial veins less defined dimension;

Vein color: Mature adaxial blend between RHS 146A and RHS 187A, mature primary and secondary abaxial veins between RHS N186C and RHS 187B;

Petiole: Sarcous; concavo-convex to involute; petiole attitude upright to semi-outright; average of about 96 cm in length, about 25 mm deep at base, about 22 mm across laterally at base and 6 mm across at blade; glaucous abaxial and adaxial;

Petiole color: Abaxial nearest N186A, between adaxial surface between 189A; in color on the inner surface, 5 cm in diameter and 8 cm in length, glabrous on both surfaces and glossy surface on the outer surface.

Inflorescence description: Spadix with spathe; female portion proximal to male portion on same peduncle; beginning to bloom about mid-August once plants are mature; producing typically four inflorescences per leaf axil.

Inflorescence bud: Linear to clavate with swollen rounded base; apex narrowly acute; about 18.0 cm long and about 2.2 cm wide in swollen base;

Bud color: Variable; nearest RHS N186D in distal areas and RHS N186B in swollen base;

Inflorescence size: Average of about 21.0 cm in length and 2.5 cm wide in female portion and 1.7 cm wide in male portion;

Flower fragrance: None detected;

Lastingness of inflorescence: About 2 to 3 weeks.

Flower quantity: Average of about 200 female sessile flowers sessile to spadix; average about 500 sessile male flowers per spadix;

Spathe: Hooded involute bract; subtending spadix and completely enveloping spadix; lanceolate; with acute apex and truncate base; margin entire;

Spathe size: Average of about 20.5 cm in length, about 9.0 cm in width if unrolled and 17.0 mm diameter at base when rolled;

Spathe color: Abaxial nearest RHS 186D; adaxial proximally nearest RSN186D and distally nearest RHS 187A;

Spadix: Male portion with acute apex, average about 4.5 cm in length and 5 mm in width, color nearest RHS 161D; female portion ellipsoidal in shape, an average of 3.5 cm in length and 15.0 mm in width, color nearest RHS 161D;

Reproductive organs: Have not been observed to develop;

Fruit and seed: Have not been observed;

Diseases and resistance: Resistance to pests and diseases beyond that common for other *Colocasia* cultivars has not been observed. The plant is tropical and grows best with ample moisture, good drainage and warm temperatures. The complete hardiness of the new plant has not been tested.

It is claimed:

1. A new and distinct cultivar of *Colocasia* plant named 'Black Swan' as herein illustrated and described.

* * * * *